United States Patent
Kiviniemi et al.

(10) Patent No.: US 8,082,030 B2
(45) Date of Patent: Dec. 20, 2011

(54) METHOD, USER-SPECIFIC PERFORMANCE MONITOR, SYSTEM, AND COMPUTER SOFTWARE PRODUCT

(75) Inventors: Antti Kiviniemi, Oulu (FI); Hannu Kinnunen, Oulu (FI); Arto Hautala, Oulu (FI); Mikko Tulppo, Oulu (FI)

(73) Assignee: Polar Electro Oy, Kempele (FI)

( * ) Notice: Subject to any disclaimer, the term of this patent is extended or adjusted under 35 U.S.C. 154(b) by 925 days.

(21) Appl. No.: 11/789,425

(22) Filed: Apr. 24, 2007

(65) Prior Publication Data
US 2007/0287928 A1 Dec. 13, 2007

(30) Foreign Application Priority Data
May 3, 2006 (FI) .................................... 20065286

(51) Int. Cl.
*A61B 5/024* (2006.01)
(52) U.S. Cl. ........................................................ 600/520
(58) Field of Classification Search .................. 600/520; 482/9
See application file for complete search history.

(56) References Cited

U.S. PATENT DOCUMENTS

| | | | |
|---|---|---|---|
| 4,281,663 A | 8/1981 | Pringle | |
| 5,706,822 A | 1/1998 | Khavari | |
| 6,132,337 A * | 10/2000 | Krupka et al. | 482/8 |
| 6,212,427 B1 | 4/2001 | Hoover | |
| 2002/0156386 A1 * | 10/2002 | Dardik et al. | 600/520 |
| 2006/0004265 A1 | 1/2006 | Pulkkinen et al. | |

FOREIGN PATENT DOCUMENTS

| | | |
|---|---|---|
| EP | 1 159 989 | 12/2001 |
| EP | 1 236 434 | 9/2002 |
| EP | 1 473 655 | 11/2004 |
| WO | WO 01/87426 | 11/2001 |
| WO | WO 02/39363 | 5/2002 |
| WO | WO 2004/109575 | 12/2004 |
| WO | WO 2005/032363 | 4/2005 |

OTHER PUBLICATIONS

Holger Oelschlager, European Communication Pursuant to Article 94(3) EPC for corresponding European Application No. 07 106 930. 6, pp. 1-5, Jul. 16, 2010.

* cited by examiner

*Primary Examiner* — Kennedy J Schaetzle
(74) *Attorney, Agent, or Firm* — Hoffmann & Baron, LLP (57) ABSTRACT

The invention relates to a method, equipment implementing the method, and a computer software product, the method generating exercise instructions for a physical exercise. The method comprises determining the standard condition value of a heart rate parameter in a user-specific performance monitor by measuring the user's heart rate wherein the standard condition value of the heart rate parameter is a function of the standard condition value of the heart rate variation; performing comparison between the standard condition value of the heart rate parameter and a standard condition reference value of the heart rate parameter; and generating exercise instruction information for at least one future physical exercise on the basis of the comparison.

28 Claims, 5 Drawing Sheets

METHOD, USER-SPECIFIC PERFORMANCE MONITOR, SYSTEM, AND COMPUTER SOFTWARE PRODUCT

CROSS-REFERENCE TO RELATED APPLICATION

This application claims priority to Finnish Patent Application Serial No. 20065286, filed on May 3, 2006, which is incorporated herein by reference.

BACKGROUND OF THE INVENTION

1. Field of the Invention

The invention relates to a method for generating exercise instructions for a physical exercise, a user-specific performance monitor, a system for generating exercise instructions for a physical exercise, and a computer software product.

2. Description of the Related Art

The aim of exercise instructions for a physical exercise is typically to achieve optimal physical condition for a person doing keep-fit exercise or for a competing athlete. The exercise instructions are typically included in a training program prepared by trainers, for example. Training programs typically define training parameters aimed at, such as the time, duration and intensity of the exercise.

Training programs are typically prepared according to the type of sport for a longer period of time in advance, based on the advance information on the effects of the particular training program on physical condition. Modification of the training program is typically based on follow-up of physical condition taking place infrequently in test exercises monitored by the trainer or by measuring ultimate performance for instance in competitive situations.

It is known that physical exercises that are heavy with respect to their intensity can quickly build up maximum physical condition, but heavy exercises repeated too often may result in overexertion instead of build-up of physical condition. The optimal amount of heavy exercise may be different with different persons. Studies on physical education have shown that the build-up of physical condition with the same exercise program may vary a great deal between different persons. A training program that has built up the physical condition of some people has provided a negative change in the physical condition or no change at all for some test persons.

A long-term training program and infrequent follow-up according to known methods are not capable of producing real-time information on the basis of which the training program could be optimized to achieve user-specifically as good physical condition as possible. Thus, it is worthwhile to consider expedients with which to generate exercise instructions for a physical exercise.

SUMMARY OF THE INVENTION

An object of the invention is to implement a method, a user-specific performance monitor, a system and a computer software product in such a way that user-specific generation of exercise instructions is achieved. As a first aspect of the invention, the invention provides a method for generating exercise instructions for a physical exercise, the method comprising: determining the standard condition value of a heart rate parameter in a user-specific performance monitor by measuring the user's heart rate; performing comparison between the standard condition value of the heart rate parameter and a standard condition reference value of the heart rate parameter; and generating exercise instruction information for at least one future physical exercise on the basis of the comparison.

A second aspect of the invention provides a user-specific performance monitor, comprising a heart rate measurement unit for measuring the user's heart rate; a heart rate parameter determination unit for determining the standard condition value of a heart rate parameter on the basis of the user's heart rate; a comparison unit for performing comparison between the standard condition value of a heart rate parameter and a standard condition reference value of the heart rate parameter; and an instruction determination unit for generating exercise instruction information for at least one future physical exercise on the basis of the comparison.

As a third aspect of the invention, the invention provides a system for generating exercise instructions for a physical exercise, comprising: heart rate parameter value determination means for determining the standard condition value of a heart rate parameter by measuring the user's heart rate in a user-specific performance monitor; comparison means for performing comparison between the standard condition value of the heart rate parameter and a standard condition reference value of the heart rate parameter; and instruction-generating means for generating exercise instruction information for at least one future physical exercise on the basis of the comparison.

As another aspect of the invention, the invention provides a computer software product comprising coded instructions for executing a computer process in a digital processor, which computer process generates exercise instructions for a physical exercise, the computer process comprising: inputting heart rate information measured in a user-specific performance monitor; determining the standard condition value of a heart rate parameter on the basis of the heart rate information; performing comparison between the standard condition value of the heart rate parameter and a standard condition reference value of the heart rate parameter; and generating exercise instruction information for at least one future physical exercise on the basis of the comparison.

Preferred embodiments of the invention are described in the dependent claims.

The invention is based on the idea that the user's response to preceding exercises is determined by measuring a standard condition heart rate parameter, the heart rate parameter being compared with a reference value of the heart rate parameter. On the basis of the comparison, an exercise instruction concerning a future exercise is determined.

The method, user-specific performance monitor, system and computer software product according to the invention provide several advantages. One advantage is obtaining a user-specific optimized or nearly optimized exercise instruction that takes into account the exertion caused by previous exercises.

BRIEF DESCRIPTION OF THE DRAWINGS

The invention will now be described in greater detail in connection with preferred embodiments, referring to the attached drawings, in which.

DETAILED DESCRIPTION OF THE PREFERRED EMBODIMENTS

Figure 1:
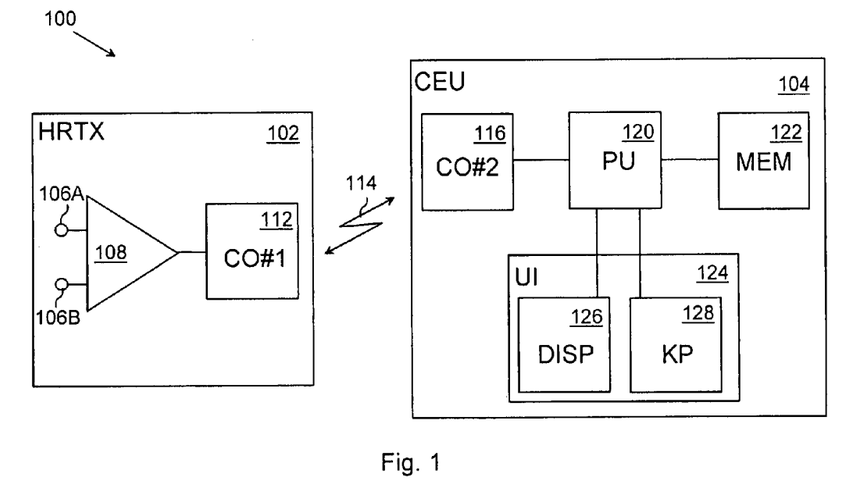
FIG. 1 shows a first example of the structure of a performance monitor.

FIG. 1 shows an example of the structure of a user-specific performance monitor 100. In this context, the user-specific performance monitor is referred to as 'performance monitor'. The performance monitor 100 typically comprises electrodes 106A, 106B, and ECG preamplifier 108 (ECG, electrocardiogram), a first communication unit (CO#1) 112, a second communication unit (CO#2) 116, a processing unit (PU) 120, a memory unit (MEM) 122 and a user interface (UI) 124.

The electrodes 106A, 106B detect the electric potential difference generated by the electric activity of the heart muscle and generate an ECG signal characterizing the electric activity of the heart muscle. The ECG signal is fed to the ECG preamplifier 108 from the electrodes 106A, 106B.

The ECG preamplifier 108 preamplifies the ECG signal and feeds the preamplified ECG signal to the first communication unit 112. The first communication unit 112 may comprise several successive amplifier stages, such as AGC (Automatic Gain Control) amplifier and a power amplifier.

The first communication unit 112 generates a signal 114 transferring ECG information. The ECG information may, for example, use the ECG as such, part of the ECG and/or timing information of the heart rate. The timing information may contain a timing pulse that predicts the timing of a predetermined part of the ECG.

The signal 114 transferring ECG information is an electromagnetic wave propagating in the air or in a conductor, for instance.

The second communication unit 116 receives the signal 114 transferring ECG information and feeds the ECG information to the processing unit 120, which executes a computer process according to the coded instructions stored in the memory unit 122.

The processing unit 120 may be implemented by using analogue circuits, ASIC circuits (Application Specific Integrated Circuit), a digital processor, memory, and computer software. The processing unit 120 may form part of the computer of the measuring unit 100.

The user interface 124 typically comprises a display unit (DISP) 126 and a display controller. The display unit 126 may contain LCD components (Liquid Crystal Display), for instance. The display unit 126 may display the exercise instructions to the user graphically and/or numerically.

The user interface 124 may further comprise a keypad (KP) 128, by means of which the user may feed commands to the performance monitor 100.

The performance monitor 100 shown in FIG. 1 may be divided into a heart rate transmitter (HRTX) 102 and a central processing unit (CEU) 104. The heart rate transmitter 102 typically comprises device parts 106A to 112 and performs ECG measurement and transmission of ECG information to the central processing unit 104. In some embodiments, the heart rate transmitter 102 may comprise a heart rate detector, which detects a predetermined part of the ECG, generates the transmitter burst representing timing of a predetermined part of the ECG and/or bit stream, and transmits the transmitter burst to the central processing unit 104 or, for example, to the second communication unit 116 positioned in the server.

The central processing unit 104 typically comprises device parts 116 to 128, which process the signal 114 transmitting ECG information and implement the user interface. Further, the central processing unit 104 may comprise a measurement module that may carry out measurements, such as acceleration measurements, temperature measurements, pressure measurements and/or positioning measurements.

The central processing unit 104 is a wrist device, for example.

Figure 2:
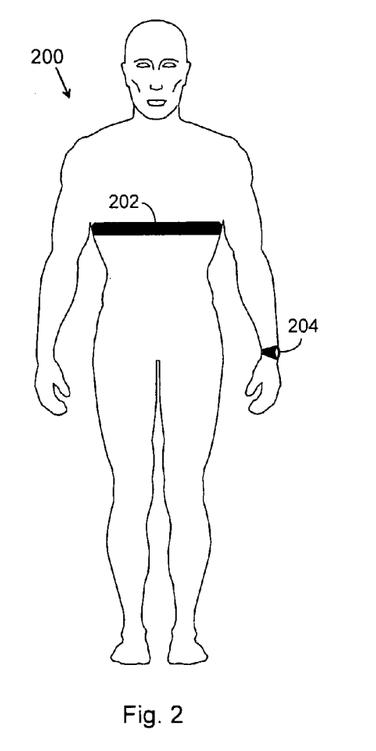
FIG. 2 shows a second example of the structure of a performance monitor.

Referring to the embodiment of FIG. 2, the heart rate transmitter 102 is positioned in a transmitter belt 202 around a user's 200 chest. The ECG information may be transmitted telemetrically, optically or galvanically from the heart rate transmitter 202 to a central processing unit 204 that may be a wrist device positioned around the user's wrist. However, the presented solution is not restricted to a wrist device.

Referring to FIG. 1 again, in one embodiment the heart rate transmitter 102 and the central processing unit 104 are integrated into the same performance monitor 100, which forms a performance monitor held around the user's wrist or around the handlebars of a bicycle. In such a case, it may be that some device parts shown in FIG. 1, such as the first communication unit 112 and the second communication unit 116 are not needed. In one embodiment, the heart rate transmitter 102 and part of the central processing unit 104 are integrated into the transmitter belt 202, whereby the transmitter belt 202 may collect ECG data, process ECG data and determine values of variables characterizing the heart rate. In this case, the signal 114 transferring ECG information transmits processed information, such as values of variables characterizing the heart rate and commands given by the user, between the heart rate transmitter 202 and the central processing unit 204.

Figure 3:
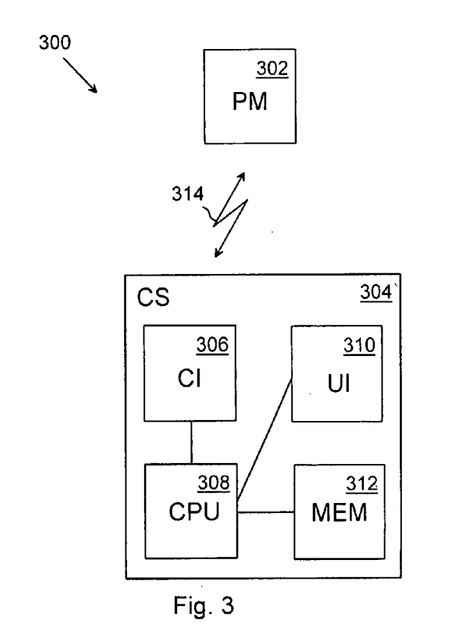
FIG. 3 shows a first example of a system for generating exercise instructions for a physical exercise.

Referring to the example of FIG. 3, a system 300 may comprise a performance monitor (PM) 302 and a calculation system (CS) 304. The performance monitor 302 may exchange exercise information, such as primary heart rate information, standard condition heart rate parameters and standard condition reference values of a heart rate parameter, with the calculation system 304 via an exercise information signal 314. Primary heart rate information comprises, for example, part of an ECG signal or timing information of the ECG.

The calculation unit 304 typically comprises a communication interface (CI) 306, a central processing unit (CPU) 408, a memory unit (MEM) 312 and a user interface.

The communication interface 306 implements the reception and possibly transmission of an exercise information signal 314. The communication interface 306 is, for instance, a wireless interface, such as a radio interface, optical interface or audio interface. In one embodiment, the communication interface 306 is a cable interface.

The central processing unit 308 executes a computer process according to the coded instructions stored in a memory unit 312 to generate exercise instructions for a physical exercise. The central processing unit 308 may feed the results of the processing, such as exercise instruction information, to an interface 310.

The calculation system 304 may be implemented by means of a computer and software, for example. The communication interface 306 may be integrated into the calculation system, or it may be a peripheral device to be connected to the calculation system.

Further, the calculation system 304 may be implemented by means of a portable communication device, such a mobile phone or a PDA device (Personal Digital Assistant).

Figure 4:
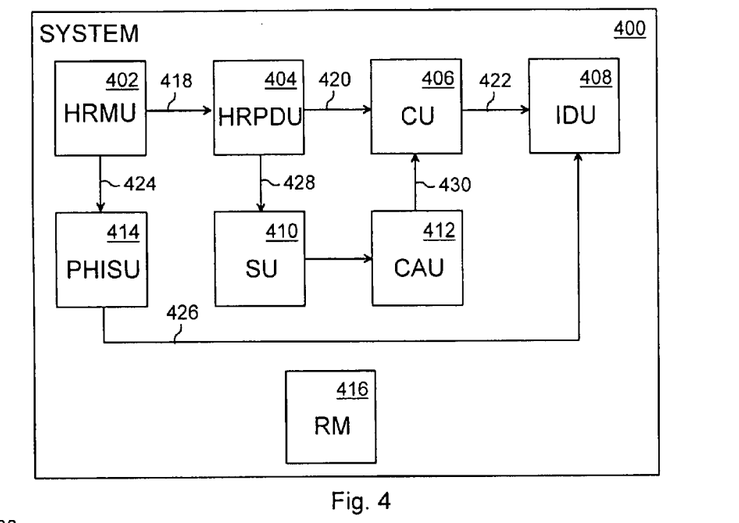
FIG. 4 shows a second example of a system for generating exercise instructions for a physical exercise.

Referring to FIG. 4, a system 400 is examined which comprises a heart rate measurement unit (HRMU) 402, a heart rate parameter determination unit (HRPDU) 404, a comparison unit (CU) 406 and an instruction determination unit (IDU) 408.

The heart rate measurement unit 402 measures the user's heart rate, for example on the basis of the detection of the ECG signal described in connection with FIG. 1, and generates a heart rate information signal 418. The heart rate information signal 418 contains heart rate information on the user's heart rate. Heart rate information may be, for instance, timing information of heart rates or information on the heart rate frequency, heart rate interval or heart rate variation.

The heart rate measurement unit 402 feeds the heart rate information signal 418 to the heart rate parameter determination unit 404, which determines the standard condition value of a heart rate parameter on the basis of the heart rate information signal 418.

A standard condition heart rate parameter characterizes the heart rate of the person being the object of the heart rate measurement in standard conditions. Standard conditions refer to the physiological state of the person being the object of the heart rate measurement in such a way that the state remains the same or nearly the same in repetitions. Thus, standard condition heart rate parameters, determined under the same standard conditions, are mutually comparable and may form a series of measurements representing the development of the heart rate parameter.

Standard conditions may be based on the user's passive action. Thus, heart rate information of the period of several hours, for example, is fed to the heart rate parameter determination unit 404, of which information the heart rate parameter determination unit 404 determines the part corresponding to standard conditions and uses this part for determining a standard condition heart rate parameter. Let us take an example where the period of time includes an exercise and the following rest period, such as night. Thus, the heart rate parameter determination unit 404 may deduce the prevailing standard conditions on the basis of the characteristics of the heart rate or the time measured, and use the corresponding part of the heart rate information for determining a standard condition heart rate parameter. In one embodiment, a standard condition heart rate parameter is determined when the person being the object of the heart rate measurement has just woken up. Standard conditions may also comprise a predetermined position of the person, such as standing position.

Standard conditions may also be based on the user's active action. Thus, the person being the object of the heart rate measurement may, in a desired state, start the heart rate measurement and the determination of a standard condition heart rate parameter. In one embodiment, the system 400 comprises reminder means (RM) 416 that remind the user about the prevailing standard conditions and starting of the measurement. The reminder means 416 may also remind the person to prepare for the standard conditions and to start the measurement.

Standard conditions may also be recognized on the basis of the user's activity, the direction of the gravitation field or the direction of the magnetic field of the earth, for example. The user's activity and/or the direction of the gravitation field may be assessed by means of, for instance, an acceleration sensor positioned in connection with the performance monitor 100.

A standard condition heart rate parameter characterizes the response of the person being the object of the heart rate measurement to an exercise.

An exercise is typically a physical action by the user, aiming at maintaining or affecting the user's physical performance. An exercise is a physical exercise, such as a walking, swimming or cycling exercise, the invention not being restricted to these exercises.

In one embodiment, the standard condition value is the function of the standard condition value of the heart rate variation. The standard condition heart rate variation characterizes the variability between successive heart rate intervals. Heart rate variation is also called heart rate variability HRV. The standard condition heart rate variation may be determined with a method according to prior art by using a Fourier and/or autoregressive analysis, for instance.

The standard condition value 420 of a heart rate parameter is fed to the comparison unit 406, which performs comparison between the standard condition value 420 of the heart rate parameter and a standard condition reference value of the heart rate parameter.

The comparison unit 406 feeds a comparison result 422 characterizing the comparison to the instruction determination unit 408 that generates exercise instruction information for at least one future exercise on the basis of the comparison.

Exercise instruction information comprises instructions for carrying out a future exercise, intended for the person being the object of the heart rate measurement. Exercise instruction information comprises, for example, a recommendation on the time, duration and intensity of the future exercise, the type of the exercise, the range of the heart rate or the energy consumption. Exercise instruction information may be presented with, for example, a weighted exertion index, in which different ranges of the heart rate are weighted with coefficients specific to particular ranges of the heart rate.

The type of the exercise may be, for instance, an anaerobic exercise, aerobic exercise or strength exercise.

In one embodiment the future exercise is, relative to the preceding exercise, the one following immediately. Exercise instruction information may comprise an instruction for a rest period, so that in this context the exercise may also be a rest exercise.

In one embodiment, the system 400 comprises a storing unit 410 and a calculation unit 412.

The storing unit 410 receives several day-specific standard condition values 428 of a heart rate parameter and stores the day-specific standard condition values 428 of the heart rate parameter. The calculation unit 412 calculates a standard condition reference value 430 of the heart rate parameter by using the standard condition day-specific values 428 of the heart rate parameter, and feeds the standard condition reference value 430 of the heart rate parameter to the comparison unit 406.

The day-specific values 428 of the standard condition heart rate parameter may be values of standard condition heart rate parameters that are measured on successive mornings in standing position. The calculation unit 412 may calculate an average value, for example, of the day-specific values 428 of the standard condition heart rate parameter. The reference value may be the average value or a modified average value obtained from the average value and, for example, standard deviation. In one embodiment, the reference value is the average value minus standard deviation.

Figure 5A:
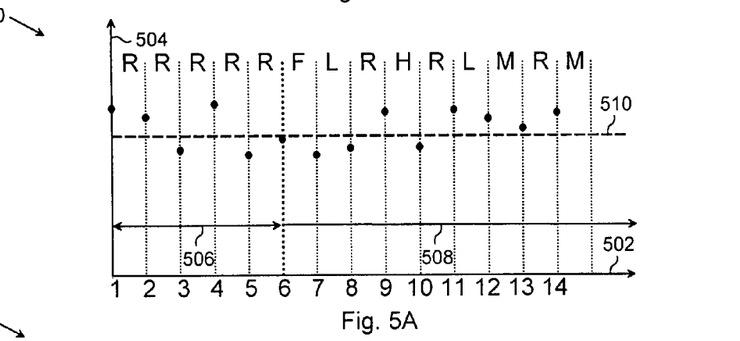
FIG. 5A shows a first example of an exercise information table.

With reference to FIG. 5A, an example of an exercise information table 500 is examined which explains the example of the operation of an instruction determination unit 508. The black dots in the exercise information table 500 denote standard condition values of a heart rate parameter. A horizontal axis 502 shows time in a random unit, and a vertical axis 504 shows the value of the heart rate parameter in the random unit. Symbols F, R, L, M and H show exercise instruction information FREE, REST, LIGHT EXERCISE, MEDIUM HEAVY EXERCISE and HEAVY EXERCISE in this order.

The exercise information table 500 of the example shows periods 1 to 14, where at the beginning of each there is a vertical broken line denoting the standard condition heart rate variation determined at the beginning of period 1 to 14.

In the example presented, the standard condition reference value 510 of the heart rate variation is determined during an initialization period 506, whereby the exercise instruction is REST. Before the exercise of each rest period 1 to 5, such as on the morning of the rest period 1 to 5, the day-specific standard condition heart rate variation is measured and stored in the storing unit 410.

In one embodiment, the standard condition reference value 510 of the heart rate variation is calculated during a flexible time period preceding the current moment of time and known in advance. The time period known in advance is for example 10 days, whereby the standard condition heart rate variations measured during the last 10 days are used in calculating the standard condition reference value 510 of the heart rate variation. The standard condition reference value 510 of the heart rate variation may be updated every time new standard condition heart rate variation is determined.

Figure 5B:
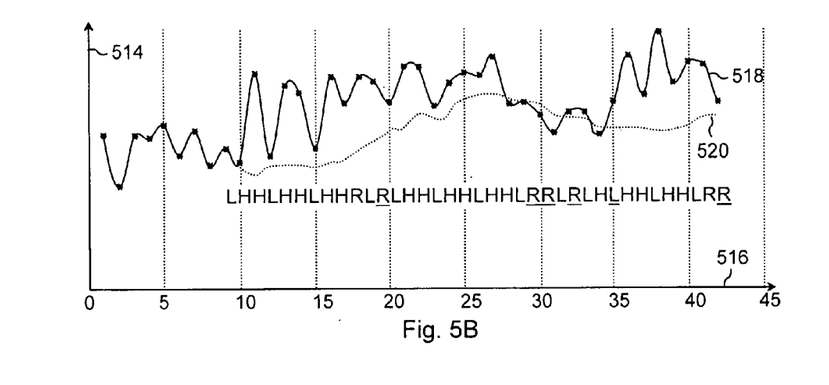
FIG. 5B shows a second example of an exercise information table.

With reference to FIG. 5B, a second example of an exercise information table 512 is examined which is based on measurements on test persons. In the example shown, the horizontal axis 516 indicates time as days, and the vertical axis 514 indicates the natural logarithm (lnHF) of the heart rate variation. A curve 518 shows the natural logarithm of the measured heart rate variation, and a curve 520 shows the reference value of the heart rate variation. The letter codes determining the exercise instruction below the curves 518, 520 are as follows: L=light exercise, H=heavy exercise, R=rest.

The training program has been preceded by a period of eight days when there has been no training. The training instruction for the period preceding the training was rest. During this period and the following training program, the test person measures the heart rate variation in standing position for five minutes after waking up in the mornings. The values of the heart rate variation are indicated on the curve 518. The actual training is started on the ninth day with light training including light jogging for 40 minutes, the heart rate average being 65% of the maximum value. This corresponds to 120 to 130 heartbeats/min with the test person. The next day, training is continued with heavy exercise including 5 minutes of warm-up, 30 minutes of energetic running, the aim of the heart rate average being 85% of the maximum heart rate, which corresponds to about 160 to 170 heartbeats/min, and finally 5 minutes of warm-down. The starting point for the training program is that it is implemented from the ninth day onwards with the sequence L-H-H-L-H-H-L-H-H-R, but from the eleventh day onwards it is changed to be lighter if the heart rate variation decreases systematically or if the heart rate variation is low. The reference value is the average of the lnHF values measured during the preceding ten days minus the standard deviation calculated from the same values. In these situations, if the training the day before has been heavy, the instruction is light training, and if the training the day before has been light, the instruction is a rest day. A supplementary condition may be to have a rest day at least every ten days and to have light training as the training instruction after two rest days, irrespective of the heart rate variation.

The training instruction has been changed from the original rhythm on five days in total. The changed exercise instructions have been underlined. For example, on the $15^{th}$ day, the heart rate variation decreases the second time in succession, whereby the instruction is an easy day. On the $20^{th}$ day, the heart rate variation decreases the second time in succession, whereby the instruction is a rest day. On the $28^{th}$ and $29^{th}$ days, the heart rate variation is below the reference value, whereby the instruction is a rest day. On the $34^{th}$ day, the heart rate variation is below the reference value, whereby the instruction is light training. On the $42^{nd}$ day, the heart rate variation decreases the second time in succession, whereby the instruction is a rest day.

When examining the training program drafted for this person and the one put into practice by him/her, it can be noted that the number of heavy exercises is slightly smaller than in the original program L-H-H-L-H-H-L-H-H-R and that the time of the heavy exercises has slightly changed from the original plan. The user of the method of the solution according to the invention can gain benefit from the fact that heavy exercises may be done at such a time when his/her system withstands a heavy exercise and the exercise thus leads to positive changes in the system with regard to build-up of performance and physical condition. On the other hand, the invention may encourage the user to do light exercise or to have a rest day when a low or decreased heart rate variation is detected.

Measurements on tests persons indicate that there may be great variations between persons having been training according to a program corresponding to the original instructions with regard to the change in physical condition, so that with some people the physical condition gets worse, whereas the group having been training according to the program of the invention may achieve a significantly better change in physical condition.

Referring to FIG. 4 again, the calculation unit 412 calculates the standard condition reference value 510 of the heart rate variation and feeds this reference value 510 to the comparison unit 406. With this proceeding, the user's normal level of heart rate variation is determined.

The initialization period 506 is followed by an exercise period 508 comprising exercise instructions deviating from the exercise instruction REST.

The exercise instruction of the first period 6 of the exercise period 508 may be FREE, in which case the user can freely select the level of the exercise according to how he/she feels.

In one embodiment, the instruction determination unit 408 generates a lightened exercise instruction relative to the preceding exercise and exercise instruction if the standard condition value of the heart rate variation of the period is below the standard condition reference value 510 of the heart rate variation. The low value of the standard condition heart rate variation may be interpreted as resulting from the exertion caused by the preceding period or periods, so that a lightened exercise instruction, such as REST, LIGHT EXERCISE or MEDIUM HEAVY EXERCISE, in relation to the exercise or exercise instruction of the preceding period, may now be determined as the exercise instruction.

Still referring to FIG. 5A, period 7 is examined as an example where the standard condition value of the heart rate variation is below the standard condition reference value 510 of the heart rate variation. Thus, the exercise instruction LIGHT EXERCISE, for example, may be generated for period 7.

In one embodiment, the instruction determination unit 408 generates an exercise instruction REST if the standard condition value of the heart rate variation is below the standard condition reference value 510 of the heart rate variation for a predetermined period of time. The values of the standard condition heart rate variation of periods 7 and 8 are examined as examples, both of these values being below the standard condition reference value 510 of the heart rate variation. Thus, the exercise instruction of period 8 is REST.

In one embodiment, the exercise instruction represents an exercise toughened up in relation to the preceding exercise instruction or maintenance of the exercise instruction HEAVY EXERCISE if the standard condition value of the heart rate variation is above the standard condition reference value 510 of the heart rate variation. An example of such a case is period 9, at the beginning of which an increased heart rate variation has been measured. Thus, the exercise instruction of the period is HEAVY EXERCISE, for instance.

In one embodiment, the instruction determination unit 408 generates an exercise instruction REST if the standard condition value of the heart rate variation is below the standard condition reference value 510 of the heart rate variation in a period of time after a predetermined exercise instruction. An example of this is period 9 where the exercise instruction is HEAVY EXERCISE, whereby a value of the standard condition heart rate variation that is lower than the standard condition reference value of the heart rate variation is measured in period 10 after period 9. Thus, REST is generated as the exercise instruction for period 10.

In one embodiment, the instruction determination unit 408 generates a lightened exercise instruction in relation to the preceding exercise or exercise instruction if the standard condition value of the heart rate variation has a downward trend, even if the standard condition value of the heart rate variation were above the standard condition reference value 510 of the heart rate variation. As an example of this the standard condition values of the heart rate variation in periods 12 and 13 are examined, both of the values being above the standard condition reference value 510 of the heart rate variation. Thus, the exercise instruction for period 13 is REST.

Each exercise instruction may be associated with a target variable measured with the performance monitor 100 and characterizing the target of the exercise numerically. The target variable may be, for example, a target average heart rate, target energy consumption or target time. The above exercise instructions may be associated with, for example, the target average heart rate as follows:
LIGHT: Average heart rate about 65% of maximum heart rate
MEDIUM HEAVY: Average heart rate about 75% of maximum heart rate
HEAVY: Average heart rate about 85% of maximum heart rate.

The association and the target average heart rates may be preprogrammed to the instruction determination unit 408.

In one embodiment, the system 400 comprises an exercise information storing unit (PHISU) 414 for storing exercise history information measured with the performance monitor 100.

The heart rate measurement unit 402 feeds measurement information 424, such as values of a heart rate parameter, to the exercise information storing unit 414, which stores the measurement information as exercise history information. The exercise history information comprises measurement information 424 and time information to be associated with the measurement information.

In one embodiment, the exercise information storing unit 414 feeds exercise history information 426 to the instruction determination unit 408, which generates exercise instruction information for at least one future exercise on the basis of the exercise history information.

The exercise history information 426 may comprise, for example, average heart rate values obtained with different exercise instructions. Thus, the instruction determination unit 408 may set the user-specific target average heart rates corresponding to different exercise instructions and change values of the target average heart rates associated with the exercise instructions when the user's performance changes during the exercise program. Thus, the exercise instructions are adapted according to the user's physical condition.

In one embodiment, the heart rate measurement unit 420 is implemented by means of a heart rate transmitter 102. The heart rate parameter determination unit 404, comparison unit 406, instruction determination unit 408, storing unit 410, calculation unit 412 and exercise information storing unit 414 may be implemented with computer software executed in the processing unit 120 of the central processing unit 104 of the performance monitor 100 and stored in the memory unit 122. The reminder means 416 may be implemented with computer software executed in the processing unit 120 of the central processing unit 104 of the performance monitor 100 and stored in the memory unit 122, and with the interface 124. The reminder means 416 may be based on sound, indicator light and/or vibration.

In one embodiment, the heart rate measurement unit 402 is implemented by means of the performance monitor 302. In this case, the heart rate parameter determination unit 404, comparison unit 406, instruction determination unit 408, storing unit 410, calculation unit 412 and/or exercise information storing unit 414 may be implemented with computer software executed in the central processing unit 308 of the calculation system 304 and stored in the memory unit 312. In this embodiment, the exercise information signal 314 transmitted by the performance monitor 302 comprises heart rate information on the user's heart rate, as well as other possible information, such as time information on the ECG components or heart rate information.

In one embodiment, the heart rate measurement unit 402 and the heart rate parameter determination unit 404 are implemented with the performance monitor 302. In this case, the comparison unit 406 and instruction determination unit 408 may be implemented with computer software executed in the central processing unit 308 of the calculation system 304 and stored in the memory unit 312.

In one embodiment, the heart rate measurement unit 402, heart rate parameter determination unit 404 and comparison unit 406 are implemented with the performance monitor 302. In this case, the instruction determination unit 408 may be implemented with computer software executed in the central processing unit 308 of the calculation system 304 and stored in the memory unit 312.

In one embodiment, the storing unit 410 and calculation unit 412 may be implemented with computer software executed in the central processing unit 308 of the calculation system 304 and stored in the memory unit 312.

In one embodiment, the exercise information storing unit 414 may be implemented with computer software executed in the central processing unit 308 of the calculation system 304 and stored in the memory unit 312.

It is to be noted that the exercise instruction tables 500 and 512 in FIGS. 5A and 5B are only suggestive and that determination of the exercise instructions on the basis of a standard condition heart rate parameter may be defined in a plurality of ways.

Figure 6:
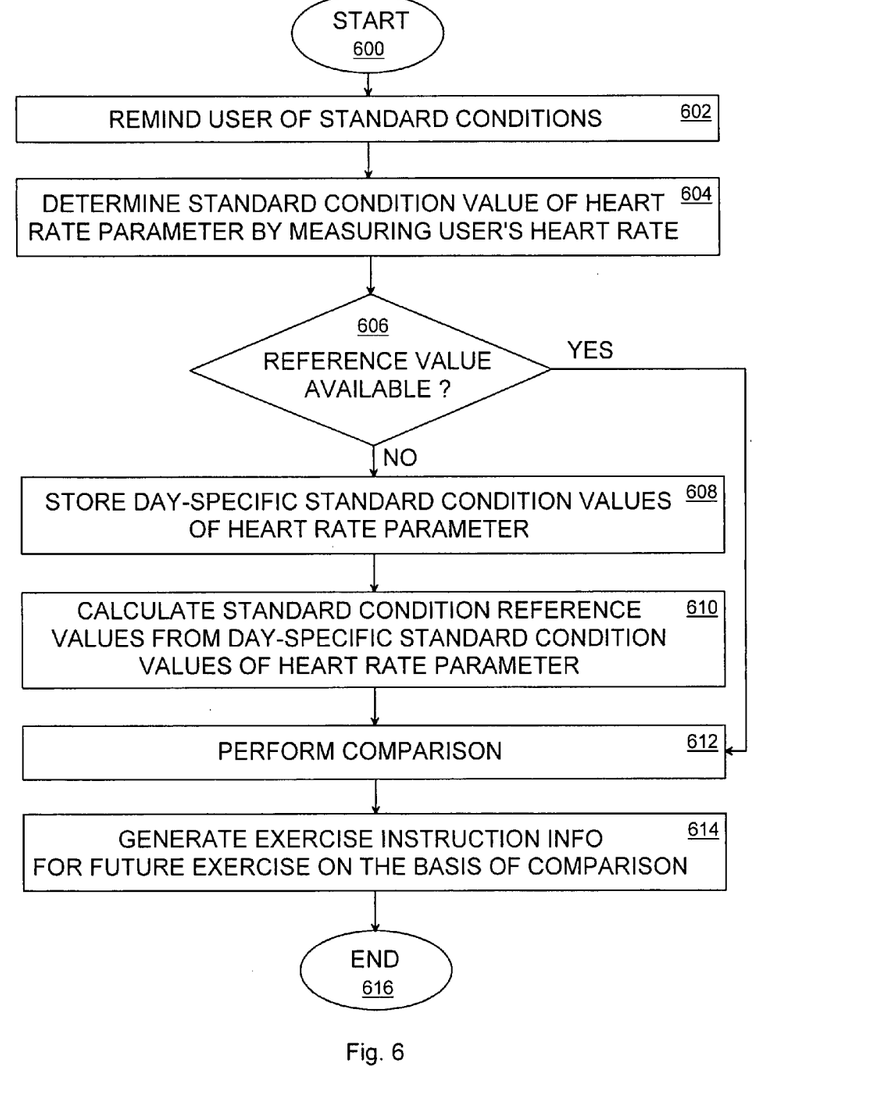
FIG. 6 shows a first example of the method according to embodiments of the invention.
Figure 7:
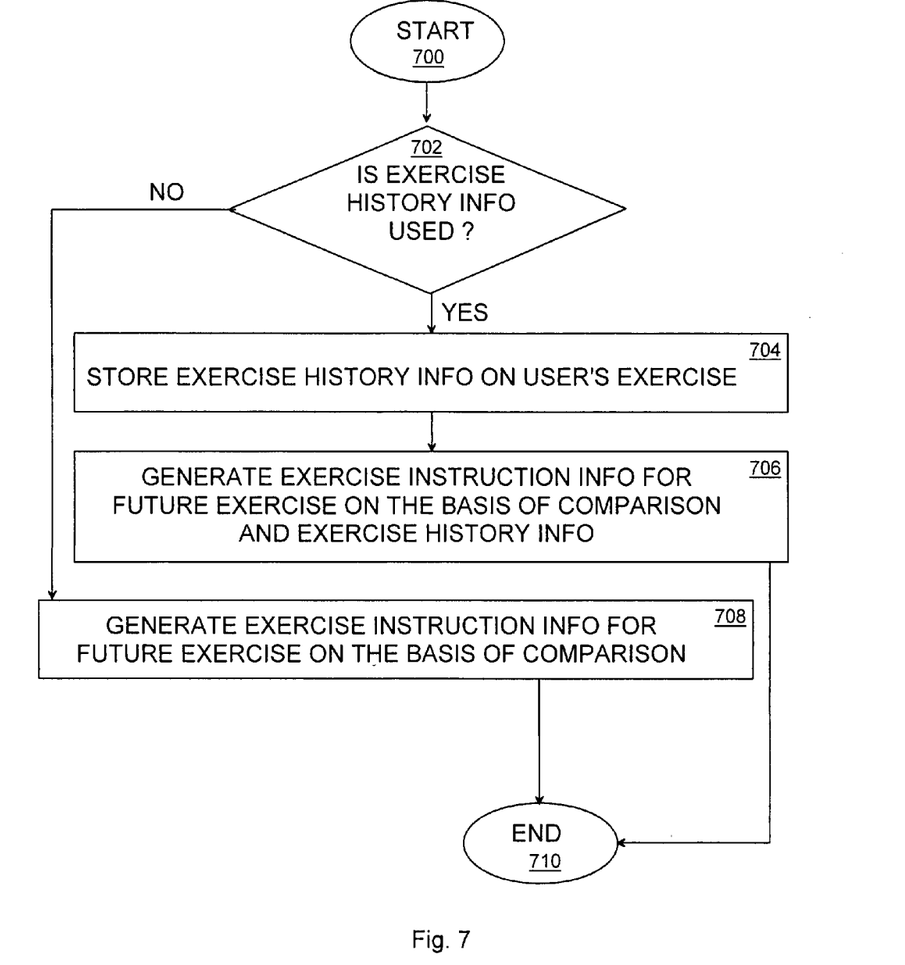
FIG. 7 shows a second example of the method according to embodiments of the invention.

With reference to FIGS. 6 and 7, let us examine methods according to embodiments of the invention.

With reference to FIG. 6, the method starts at 600.

At 602, the user is reminded, by means of the user-specific performance monitor 100, of at least one of the following: prevailing standard conditions, preparing for standard conditions.

At 604, the value of a standard condition heart rate parameter is determined in the user-specific performance monitor 100 by measuring the user's heart rate.

If, at 606, no standard condition reference value of the heart rate parameter is available, several day-specific values of the standard condition heart rate parameter are stored at 608, and a standard condition reference value of the heart rate parameter is calculated at 610 by using several day-specific values of standard condition heart rate parameters.

At 612, the standard condition value of the heart rate parameter and the standard condition reference value of the heart rate parameter are compared.

At 614, exercise instruction information is generated for at least one future exercise on the basis of the comparison.

At 616, the method ends.

With reference to FIG. 7, the method starts at 700.

If, at 702, exercise history information is used when exercise instruction information is generated, at 704 exercise history information on the user's exercise, measured with the user-specific performance monitor, is stored, and at 708 exercise instruction information is generated for said at least one future exercise on the basis of the exercise history information.

If, at 702, no exercise history information is used when exercise instruction information is generated, exercise instruction information is generated at 706 for said at least one future exercise on the basis of the comparison.

At 710, the method ends.

FIGS. 6 and 7 further determine a computer process, method steps of which may be carried out in the performance monitor 100 and/or in the calculation system 304.

Figure 8:
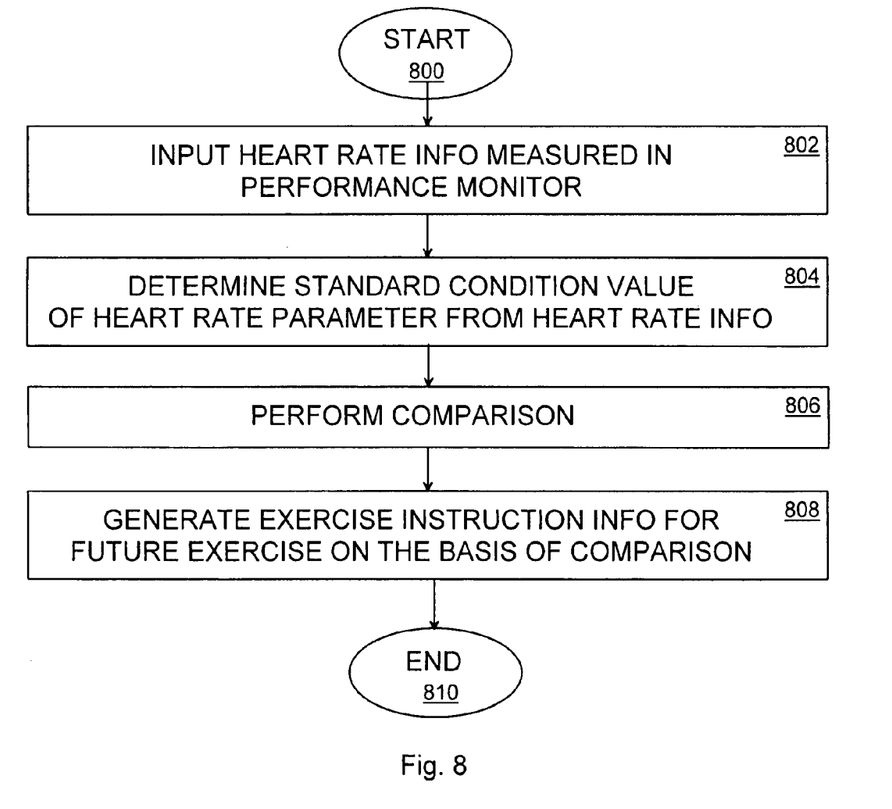
FIG. 8 shows an example of the computer process according to embodiments of the invention.

With reference to FIG. 8, let us examine a computer process according to an embodiment of the invention, which process is suitable for generating exercise instructions for a physical exercise.

The computer process starts at 800.

At 802, heart rate information measured in the user-specific performance monitor 100 is inputted.

At 804, the value 420 of a standard condition heart rate parameter is determined on the basis of the heart rate information.

At 806, the value 420 of the standard condition heart rate parameter and a standard condition reference value of the heart rate parameter are compared.

At 808, exercise instruction information is generated for at least one future exercise on the basis of the comparison.

At 810, the method ends.

The computer process may be included in the coded instructions executed in the processing unit 120 of the performance monitor 100 and/or in the central processing unit of the calculation system 304. The coded instructions may be stored in the memory unit 122 of the performance monitor 100 and/or in the memory unit of the calculation system 304.

The coded instructions may be included in a computer software product and they may be transferred via a distribution means. The distribution means is, for example, an electric, magnetic or optical distribution means. The distribution means may be a physical distribution means, such as a memory unit, an optical disc or a telecommunication signal.

Although the invention has been described above with reference to the example according to the attached drawings, it will be obvious that it is not restricted thereto but may be modified in a plurality of ways within the scope of the attached claims.

What is claimed is:

1. A method for generating exercise instructions for a physical exercise comprising:
   determining a standard condition value of a heart rate parameter in a user-specific performance monitor by measuring a user's heart rate, wherein the standard condition value of the heart rate parameter is a function of the standard condition value of a heart rate variation;
   performing comparison between the standard condition value of the heart rate parameter and a standard condition reference value of the heart rate parameter;
   generating exercise instruction information for at least one future physical exercise on the basis of the comparison;
   storing several day-specific standard condition values of the heart rate parameter; and
   calculating the standard condition reference value of the heart rate parameter by using several day-specific standard condition values of the heart rate parameter.

2. A method according to claim 1, further comprising:
   storing exercise history information on the user's exercise, measured with the user-specific performance monitor; and
   generating exercise instruction information for said at least one future exercise on the basis of the exercise history information.

3. A method according to claim 1, further comprising reminding the user of at least one of the following by means of the user-specific performance monitor: prevailing standard conditions, preparing for standard conditions.

4. A method according to claim 1, wherein the exercise instruction information characterizes at least one of the following features of the future exercise: time of the exercise, intensity of the exercise, duration of the exercise, type of the exercise, energy consumption of the exercise.

5. A user-specific performance monitor, comprising: a heart rate measurement unit configured to measure the user's heart rate;
   a heart rate parameter determination unit configured to determine a standard condition value of a heart rate parameter on the basis of a user's heart rate, wherein the standard condition value of the heart rate parameter is a function of the standard condition value of a heart rate variation;
   a comparison unit configured to perform comparison between the standard condition value of the heart rate parameter and a standard condition reference value of the heart rate parameter;
   an instruction determination unit configured to generate exercise instruction information for at least one future physical exercise on the basis of the comparison;
   a storing unit configured to store several day-specific standard condition values of the heart rate parameter; and
   a calculation unit configured to calculate the standard condition reference value of the heart rate parameter by using several day-specific standard condition values of heart rate parameters.

6. A user-specific performance monitor according to claim 5, further comprising:

an exercise history information storing unit configured to store exercise history information measured by means of the user-specific performance monitor; and wherein the instruction determination unit is configured to generate exercise instruction information for at least one future exercise on the basis of the exercise history information.

7. A user-specific performance monitor according to claim 5, further comprising reminder means for reminding the user of at least one of the following: prevailing standard conditions, preparing for standard conditions.

8. A user-specific performance monitor according to claim 5, wherein the exercise instruction information characterizes at least one of the following features of the future exercise: time of the exercise, intensity of the exercise, duration of the exercise, type of the exercise, energy consumption of the exercise.

9. A system for generating exercise instructions for a physical exercise comprising:

heart rate parameter value determination means for determining a standard condition value of a heart rate parameter by measuring a user's heart rate in a user-specific performance monitor, wherein the standard condition value of the heart rate parameter is a function of the standard condition value of a heart rate variation;

comparison means for performing comparison between the standard condition value of the heart rate parameter and a standard condition reference value of the heart rate parameter;

instruction-generating means for generating exercise instruction information for at least one future physical exercise on the basis of the comparison;

a storing unit configured to store several day-specific standard condition values of the heart rate parameter; and a calculation unit configured to calculate the standard condition reference value of the heart rate parameter by using several day-specific standard condition values of heart rate parameters.

10. A system according to claim 9, further comprising:

an exercise history information storing unit configured to store exercise history information measured by means of the user-specific performance monitor; and wherein the instruction determination unit is configured to generate exercise instruction information for at least one future exercise on the basis of the exercise history information.

11. A system according to claim 9, further comprising reminder means for reminding the user of at least one of the following: prevailing standard conditions, preparing for standard conditions.

12. A system according to claim 9, wherein the exercise instruction information characterizes at least one of the following features of the future exercise: time of the exercise, intensity of the exercise, duration of the exercise, type of the exercise, energy consumption of the exercise.

13. A non-transitory computer-readable storage medium, comprising instructions that, when executed by a processing device, cause the processing device to:

input heart rate information measured in a user-specific performance monitor;

determine a standard condition value of a heart rate parameter on the basis of the heart rate information, wherein the standard condition value of the heart rate parameter is a function of the standard condition value of a heart rate variation;

perform comparison between the standard condition value of the heart rate parameter and a standard condition reference value of the heart rate parameter;

generate exercise instruction information for at least one future physical exercise on the basis of the comparison;

store several day-specific standard condition values of the heart rate parameter; and calculate the standard condition reference value of the heart rate parameter by using several day-specific standard condition values of the heart rate parameter.

14. A non-transitory computer-readable storage medium according to claim 13, further comprising coded instructions that, when executed by a processing device, cause the processing device to:

store exercise history information on the user's exercise, measured with the user-specific performance monitor; and generate exercise instruction information for said at least one future exercise on the basis of the exercise history information.

15. A non-transitory computer-readable storage medium according to claim 13, further comprising coded instructions that, when executed by a processing device, cause the processing device to remind the user of at least one of the following by means of the user-specific performance monitor: prevailing standard conditions, preparing for standard conditions.

16. A non-transitory computer-readable storage medium according to claim 13, wherein the exercise instruction information characterizes at least one of the following features of the future exercise: time of the exercise, intensity of the exercise, duration of the exercise, type of the exercise, energy consumption of the exercise.

17. A method for generating exercise instructions for a physical exercise comprising:

determining a standard condition value of a heart rate parameter in a user-specific performance monitor by measuring a user's heart rate, wherein the standard condition value of the heart rate parameter is a function of the standard condition value of a heart rate variation;

performing comparison between the standard condition value of the heart rate parameter and a standard condition reference value of the heart rate parameter;

generating exercise instruction information for at least one future physical exercise on the basis of the comparison;

storing exercise history information on the user's exercise, measured with the user-specific performance monitor; and generating exercise instruction information for said at least one future exercise on the basis of the exercise history information.

18. A method according to claim 17, further comprising reminding the user of at least one of the following by means of the user-specific performance monitor: prevailing standard conditions, preparing for standard conditions.

19. A method according to claim 17, wherein the exercise instruction information characterizes at least one of the following features of the future exercise: time of the exercise, intensity of the exercise, duration of the exercise, type of the exercise, energy consumption of the exercise.

20. A user-specific performance monitor, comprising: a heart rate measurement unit configured to measure the user's heart rate;

a heart rate parameter determination unit configured to determine a standard condition value of a heart rate parameter on the basis of a user's heart rate, wherein the standard condition value of the heart rate parameter is a function of the standard condition value of a heart rate variation;

a comparison unit configured to perform comparison between the standard condition value of the heart rate parameter and a standard condition reference value of the heart rate parameter;

an instruction determination unit configured to generate exercise instruction information for at least one future physical exercise on the basis of the comparison;

an exercise history information storing unit configured to store exercise history information measured by means of the user-specific performance monitor; and wherein the instruction determination unit is configured to generate exercise instruction information for at least one future exercise on the basis of the exercise history information.

21. A user-specific performance monitor according to claim 20, further comprising reminder means for reminding the user of at least one of the following: prevailing standard conditions, preparing for standard conditions.

22. A user-specific performance monitor according to claim 20, wherein the exercise instruction information characterizes at least one of the following features of the future exercise: time of the exercise, intensity of the exercise, duration of the exercise, type of the exercise, energy consumption of the exercise.

23. A system for generating exercise instructions for a physical exercise comprising:

heart rate parameter value determination means for determining a standard condition value of a heart rate parameter by measuring a user's heart rate in a user-specific performance monitor, wherein the standard condition value of the heart rate parameter is a function of the standard condition value of a heart rate variation;

comparison means for performing comparison between the standard condition value of the heart rate parameter and a standard condition reference value of the heart rate parameter;

instruction-generating means for generating exercise instruction information for at least one future physical exercise on the basis of the comparison;

an exercise history information storing unit configured to store exercise history information measured by means of the user-specific performance monitor; and wherein the instruction determination unit is configured to generate exercise instruction information for at least one future exercise on the basis of the exercise history information.

24. A system according to claim 23, further comprising reminder means for reminding the user of at least one of the following: prevailing standard conditions, preparing for standard conditions.

25. A system according to claim 23, wherein the exercise instruction information characterizes at least one of the following features of the future exercise: time of the exercise, intensity of the exercise, duration of the exercise, type of the exercise, energy consumption of the exercise.

26. A non-transitory computer-readable storage medium, comprising instructions that, when executed by a processing device, cause the processing device to:

input heart rate information measured in a user-specific performance monitor;

determine a standard condition value of a heart rate parameter on the basis of the heart rate information, wherein the standard condition value of the heart rate parameter is a function of the standard condition value of a heart rate variation;

perform comparison between the standard condition value of the heart rate parameter and a standard condition reference value of the heart rate parameter;

generate exercise instruction information for at least one future physical exercise on the basis of the comparison;

store exercise history information on the user's exercise, measured with the user-specific performance monitor; and generate exercise instruction information for said at least one future exercise on the basis of the exercise history information.

27. A non-transitory computer-readable storage medium according to claim 26, further comprising instructions that, when executed by a processing device, cause the processing device to remind the user of at least one of the following by means of the user-specific performance monitor: prevailing standard conditions, preparing for standard conditions.

28. A non-transitory computer-readable storage medium according to claim 26, wherein the exercise instruction information characterizes at least one of the following features of the future exercise: time of the exercise, intensity of the exercise, duration of the exercise, type of the exercise, energy consumption of the exercise.

* * * * *